(12) United States Patent
Simon et al.

(10) Patent No.: US 10,588,811 B2
(45) Date of Patent: Mar. 17, 2020

(54) LOW FRICTION GEARBOX FOR MEDICAL ASSIST DEVICE

(71) Applicant: STEERING SOLUTIONS IP HOLDING CORPORATION, Saginaw, MI (US)

(72) Inventors: Daniel C. Simon, Freeland, MI (US); Patrik M. Ryne, Midland, MI (US)

( * ) Notice: Subject to any disclaimer, the term of this patent is extended or adjusted under 35 U.S.C. 154(b) by 895 days.

(21) Appl. No.: 14/700,583

(22) Filed: Apr. 30, 2015

(65) Prior Publication Data

US 2016/0317375 A1    Nov. 3, 2016

(51) Int. Cl.
*A61H 3/00* (2006.01)
*A61H 1/02* (2006.01)
(Continued)

(52) U.S. Cl.
CPC .............. *A61H 3/00* (2013.01); *A61F 2/605* (2013.01); *A61F 2/68* (2013.01); *A61H 1/0244* (2013.01); *H02K 7/1166* (2013.01); *A61F 2002/5039* (2013.01); *A61F 2002/6836* (2013.01); *A61H 2201/1215* (2013.01); *A61H 2201/149* (2013.01); *A61H 2201/1454* (2013.01); *A61H 2201/164* (2013.01); *A61H 2201/165* (2013.01); *A61H 2201/1623* (2013.01); *A61H 2201/1635* (2013.01); *A61H 2201/1676* (2013.01); *F16H 55/02* (2013.01); *F16H 2057/0213* (2013.01)

(58) Field of Classification Search
CPC ...... A61H 1/02; A61H 1/0207; A61H 1/0211; A61H 1/0237–1/0262; A61H 1/0274–1/0288; A61H 3/00; A61H 2003/007; A61H 2201/1215; A61H 2201/1454; A61H 2201/149; A61F 2/6836; H02K 7/1166
See application file for complete search history.

(56) References Cited

U.S. PATENT DOCUMENTS 7,404,782 B2   7/2008  Kudoh
7,429,253 B2   9/2008  Shimada et al.
(Continued)

FOREIGN PATENT DOCUMENTS

CN    101132753 A    2/2008
CN    102811938 A    12/2012
(Continued)

OTHER PUBLICATIONS

Chinese Office Action and Search Report for Chinese Application No. 201610276134.5 dated Jun. 26, 2017 with English Translation, 9 pages.
(Continued)

*Primary Examiner* — Valerie L Woodward
(74) *Attorney, Agent, or Firm* — Dickinson Wright PLLC

(57) ABSTRACT

In one exemplary embodiment of the present invention, a gearbox assembly for a medical assist device having a motor assembly and a leg support is provided. The gearbox assembly includes a worm configured to be operably coupled to the motor assembly, and a worm gear meshingly engaged with the worm. The worm gear is configured to be operably coupled to the leg support, and the worm and the worm gear are configured to transfer rotary motion from the motor assembly to the leg support upon initiation of a force applied to the leg support.

9 Claims, 3 Drawing Sheets

(51) Int. Cl.
*A61F 2/68* (2006.01)
*H02K 7/116* (2006.01)
*A61F 2/60* (2006.01)
*A61F 2/50* (2006.01)
*F16H 55/02* (2006.01)
*F16H 57/021* (2012.01)

(56) References Cited

U.S. PATENT DOCUMENTS

| | | | |
|---|---|---|---|
| 7,628,766 B1 | 12/2009 | Kazerooni et al. | |
| 2004/0106881 A1 | 6/2004 | McBean et al. | |
| 2006/0052731 A1 | 3/2006 | Shimada et al. | |
| 2010/0249673 A1* | 9/2010 | Nef | A61H 1/0281 601/33 |
| 2014/0276265 A1* | 9/2014 | Caires | A61H 3/00 601/34 |
| 2014/0358053 A1* | 12/2014 | Triolo | A61H 3/00 602/16 |
| 2015/0272810 A1 | 10/2015 | Teng et al. | |
| 2016/0045385 A1* | 2/2016 | Aguirre-Ollinger | A61H 3/00 623/24 |
| 2016/0045387 A1 | 2/2016 | Lee et al. | |
| 2016/0317374 A1 | 11/2016 | Simon et al. | |
| 2017/0252254 A1 | 9/2017 | Velazquez Nino | |

FOREIGN PATENT DOCUMENTS

| | | |
|---|---|---|
| CN | 103200919 A | 7/2013 |
| CN | 104068950 A | 10/2014 |
| CN | 104188675 A | 12/2014 |
| JP | 2011019669 A | 2/2011 |
| JP | 2012217746 A | 11/2012 |
| KR | 100731899 B1 | 6/2007 |
| TW | 201330843 A | 8/2013 |
| WO | 2012070244 A1 | 5/2012 |
| WO | 2013019749 A1 | 2/2013 |
| WO | 2014093470 A1 | 6/2014 |
| WO | 2014138871 A1 | 9/2014 |

OTHER PUBLICATIONS

Chinese Office Action and Search Report for Chinese Application No. 201610533896.9 dated Dec. 4, 2017with English Translation, 13 pages.
European Search Report for EP Application No. 16160267.7 dated Oct. 5, 2016.
European Search Report for EP Application No. 16163383.9 dated Oct. 6, 2016.
English Translation of Office Action regarding related CN App. No. 201610533896.9; dated Oct. 16, 2018; 11 pgs.

\* cited by examiner

LOW FRICTION GEARBOX FOR MEDICAL ASSIST DEVICE

FIELD OF THE INVENTION

The following description relates to medical assist devices and, more specifically, to a low friction gearbox for medical assist devices.

BACKGROUND

Some exoskeleton devices may be used to assist medical patients with one or more movements. For example, exoskeleton devices may be provided for the arms or legs of a user. Where a user has full use of the limb supported by the exoskeleton device, it may be used to enhance natural abilities such as load carrying. Where the user has impaired use of the limb supported by the exoskeleton device, it may be used for rehabilitative purposes or to replicate a full physical function. Such devices may be powered by one or more motors coupled to gears or pulleys configured to move a user's limb in a desired motion, such as walking.

Some exoskeleton devices may be powered by hydraulic pumps or electric motors with planetary gear systems. However, the hydraulic components may leak and require a vent valve. The electric motors with planetary gear systems may have high friction which makes it difficult to backdrive, and may have lash that results in noise and poor user feel during operation. Accordingly, it is desirable to provide new methods to power exoskeleton devices.

SUMMARY OF THE INVENTION

In one exemplary embodiment of the present invention, a gearbox assembly for a medical assist device having a motor assembly and a leg support is provided. The gearbox assembly includes a worm configured to be operably coupled to the motor assembly, and a worm gear meshingly engaged with the worm. The worm gear is configured to be operably coupled to the leg support, and the worm and the worm gear are configured to transfer rotary motion from the motor assembly to the leg support upon initiation of a force applied to the leg support.

In another exemplary embodiment of the present invention, a medical assist device is provided. The device includes a support frame including a support arm extending therefrom, a gearbox coupled to the support frame, the gearbox including a worm and a worm gear meshingly engaged with the worm, and a leg support operably coupled to the worm gear, The gearbox is configured to provide a rotational force to the leg support.

In yet another exemplary embodiment of the present invention, a medical assist device is provided. The device includes a support frame including a support arm extending therefrom, a gearbox coupled to the support frame, and a leg support operably coupled to the gearbox. The gearbox is configured to provide a rotational force to the leg support, and to be backdriveable by a force from the leg support that is greater than a force from the gearbox.

These and other advantages and features will become more apparent from the following description taken in conjunction with the drawings.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION

Figure 1:
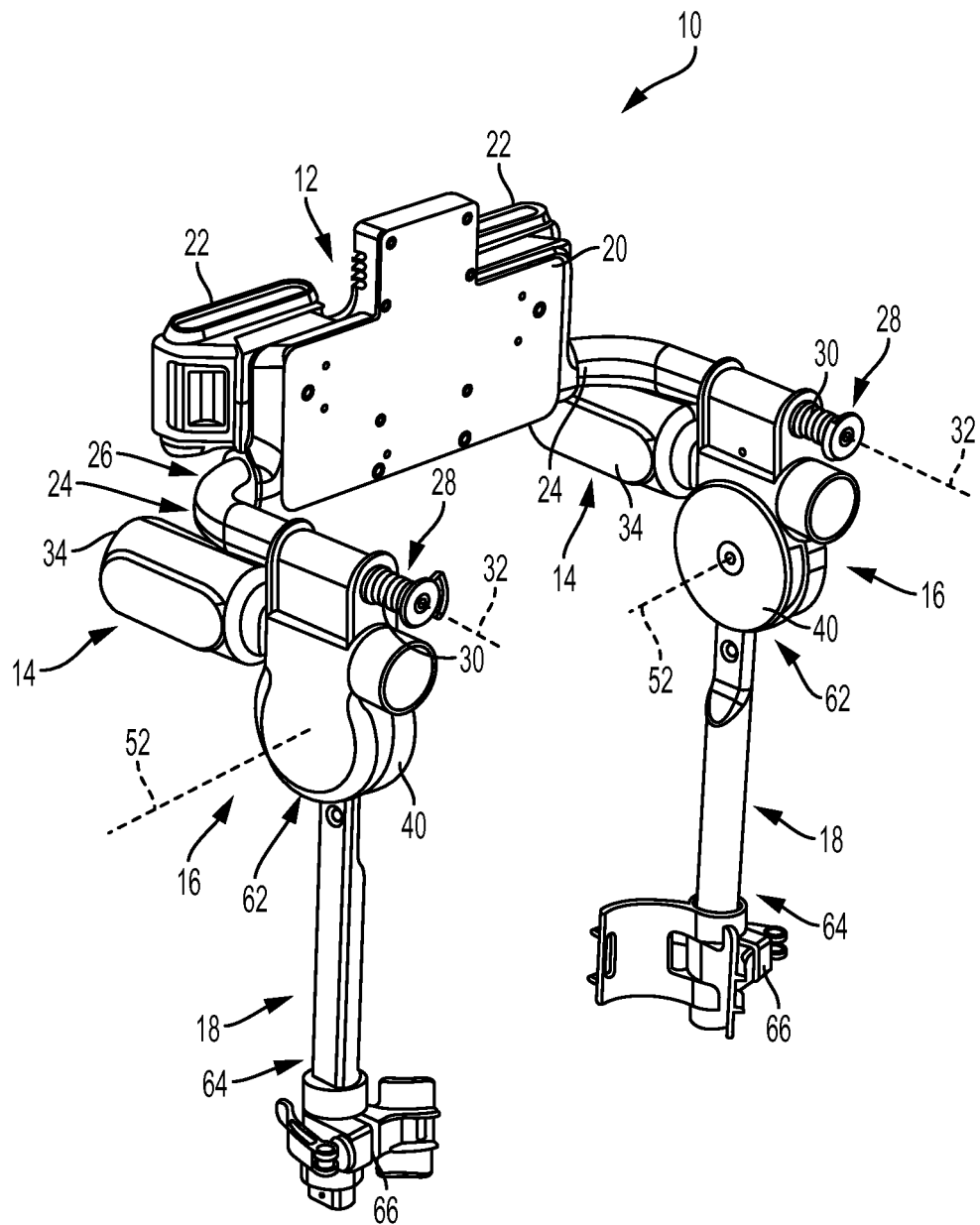
FIG. 1 is a perspective view of an exemplary adjustable medical assist device.

Referring now to the Figures, where the invention will be described with reference to specific embodiments, without limiting same, FIG. 1 illustrates an exemplary adjustable exoskeleton or medical assist device 10. In the exemplary embodiment, adjustable device 10 generally includes a support frame 12, a pair of motor assemblies 14 each respectively associated with a gearbox 16, and a pair of leg supports 18.

In the embodiment shown, motor assembly 14 is backdriveable. This allows a user of device 10 to overpower motor assembly 14 to aid in the comfort and control of device 10 by a user, as will be described hereinafter. In addition, since motor assembly 14 is an "assist" motor, it can be smaller and quieter than those previously known. The invention assists a user, but always allows the user to maintain control and is only actuated when the user initially initiates a force causing motor assembly 14 to engage and/or assist the user movement.

Support frame 12 is configured to be disposed about a user's torso or hips and includes a back support 20, one or more power source 22 (e.g., a battery), a controller (not shown), and a pair of hip supports or support arms 24 extending from back support 20. Back support 20 is configured to rest against a user's back, power source 22 is configured to power motor assembly 14, and the controller is configured to selectively control motor assembly 14 and/or movement of gearbox 16. As used herein, the term controller refers to an application specific integrated circuit (ASIC), an electronic circuit, a processor (shared, dedicated, or group) and memory that executes one or more software or firmware programs, a combinational logic circuit, and/or other suitable components that provide the described functionality.

Support arms 24 each include a proximal end 26 and a distal end 28. Proximal end 26 is coupled to back support 20, and distal end 28 includes a plurality of adjustment notches or grooves 30 formed therein. Distal end 28 extends along a longitudinal axis 32 and has a circular or generally circular cross-section.

Figure 2:
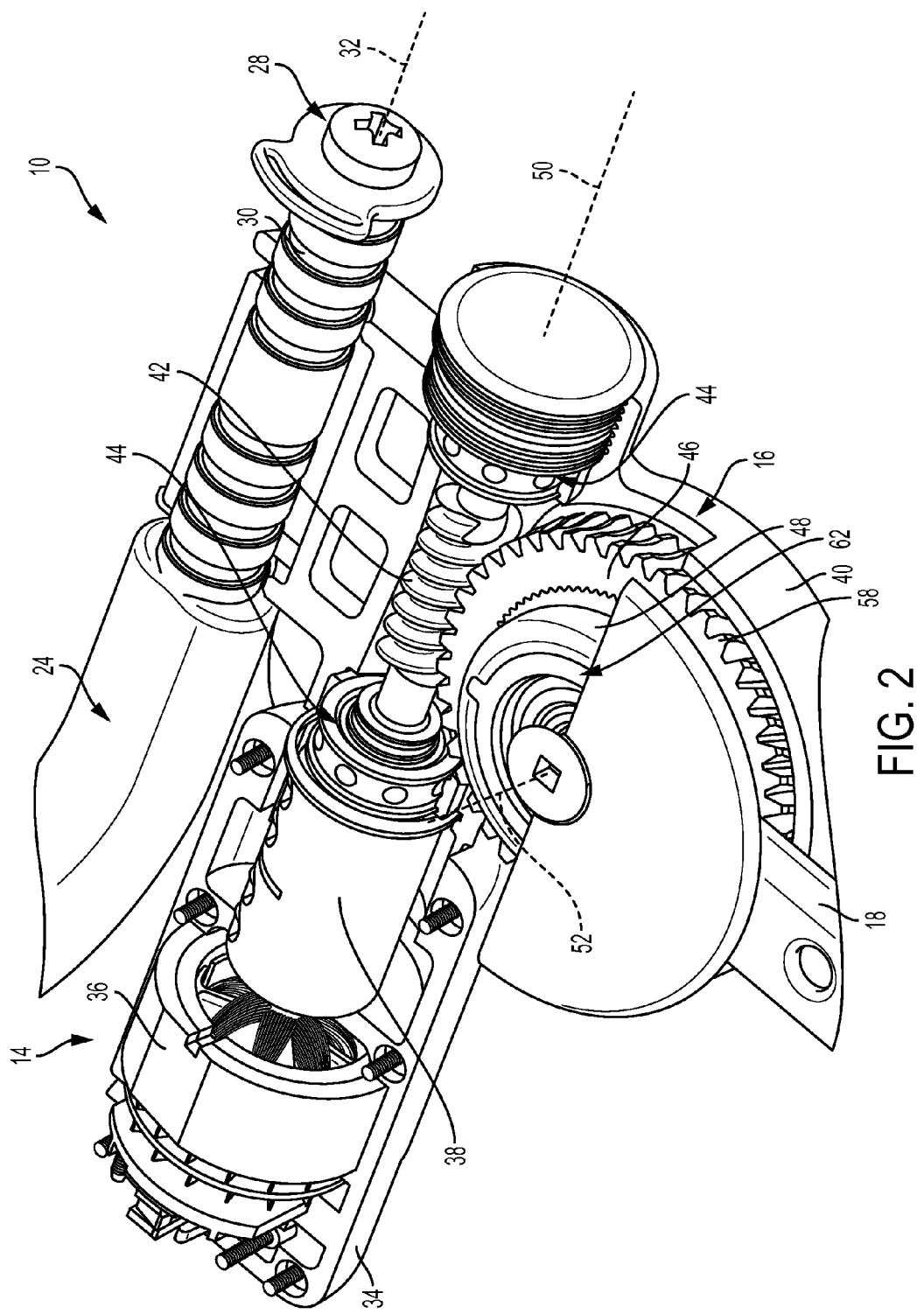
FIG. 2 is a partial sectional view of an exemplary gearbox assembly of the device shown in FIG. 1.

With additional reference to FIG. 2, in the exemplary embodiment, motor assembly 14 includes a housing 34, one or more motors 36, and an output shaft 38 operatively associated with gearbox 16. As described herein in more detail, motor assembly 14 is configured to apply a torque to gearbox 16 to selectively rotate leg support 18, thus enabling a user's hip joint to be extended or bent.

With further reference to FIG. 2, gearbox 16 is configured to assist and support a user's hip movement and generally includes a housing 40, a worm 42, bearings 44, a worm gear 46, and an adapter 48. Bearings 44 rotatably support worm 42, which is meshingly engaged to worm gear 46 to transfer rotary motion from motor 36 to leg support 18 via adapter 48. Worm 42 is configured to rotate about an axis 50, which is parallel to or substantially parallel to longitudinal axis 32. Worm gear 46 and leg support 18 are configured to rotate about an axis 52, which is orthogonal to or substantially orthogonal to axis 50. Gearbox 16 is configured to rotate about longitudinal axis 32 of an associated support arm 24 to facilitate hip flexion and extension while the pivot allows for, but does not force, hip adduction and abduction.

Gearbox 16 is configured to be reversible or backdriveable by a force from leg support 18 that is greater than a force produced by gearbox 16. For example, gearbox 16 may produce a first force in a counter-clockwise direction about axis 52. Gearbox 16 (including worm 42 and worm gear 46) is configured to be reversible in a clockwise direction about axis 52 by a second force from leg support 18 (e.g., movement of a user's leg) that is greater than the first force. As such, a user may overpower gearbox 16 to maintain control over the device rather than the device dictating the user's movement.

Figure 3:
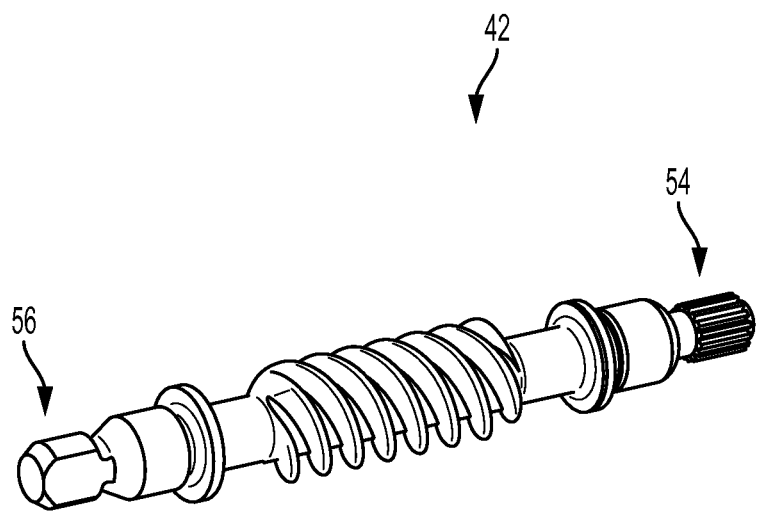
FIG. 3 is a perspective view of an exemplary worm of the gearbox assembly shown in FIGS. 1 and 2.

As shown in FIG. 3, worm 42 includes a first end 54 and an opposite second end 56. In the exemplary embodiment, first end 54 is splined and is configured to couple to motor output shaft 38. Second end 56 may be keyed for coupling to an adjacent component (not shown).

Figure 4:
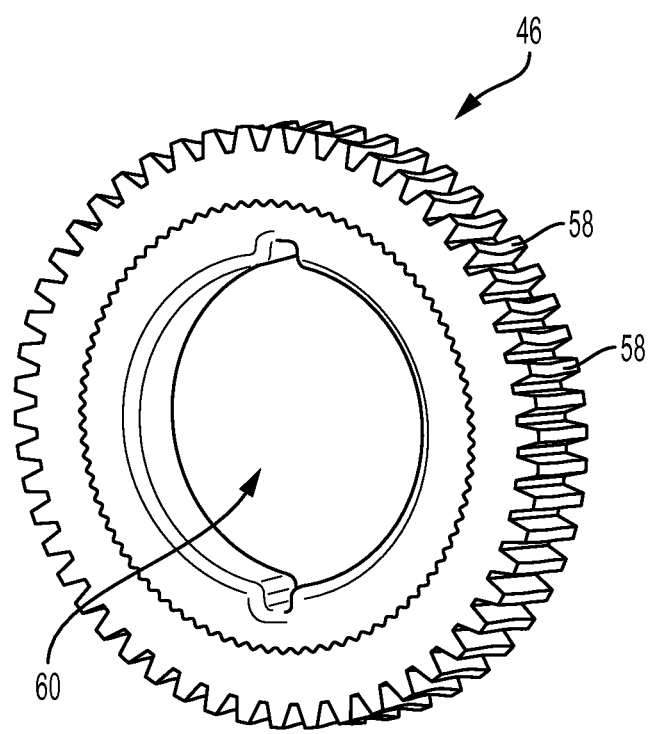
FIG. 4 is a perspective view of an exemplary worm gear of the gearbox assembly shown in FIGS. 1 and 2.

As shown in FIG. 4, worm gear 46 includes an outer diameter having a plurality of gear teeth 58 configured to meshingly engage worm 42, and an inner diameter defining an adapter aperture 60 that is keyed to receive adapter 48. In the exemplary embodiment, adapter 48 is sized and keyed to receive a portion of leg support 18 (see FIG. 2)

In the exemplary embodiment, leg support 18 is configured to support a user's upper leg and includes a proximal end 62, a distal end 64, and a leg clamp 66. Proximal end 62 is coupled to adapter 48 of gearbox 16 such that leg support 18 is rotatable about axis 52, and leg clamp 66 is coupled to distal end 64. Leg clamp 66 is configured to connect to a user's leg, for example, by a strap connected directly to clamp 66.

A method of assembling medical assist device 10 includes providing support frame 12, motor assembly 14, gearbox 16, and leg support 18. Motor assembly 14 and leg support 18 are operably coupled to the gear system of gearbox 16 to transfer rotary motion therebetween. The gear system includes worm 42, worm gear 46, and adapter 48. Support arm distal end 28 is inserted into gearbox 16.

Described herein are systems and methods for powering a medical assist device. The systems include a gearbox having a worm coupled between a motor and a worm gear to rotate a leg support of the medical assist device. As such, the system enables the use of a small motor, which reduces weight and cost of the device. The gearing system of the gearbox, low friction, includes a high gear ratio, is quiet, and is backdriveable. Additionally, the gearing system provides a low profile gearbox compared to previously known systems.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description.

Having thus described the invention, it is claimed:

1. A gearbox assembly for a medical assist device having a motor assembly and a leg support, the gearbox assembly comprising:
   a worm configured to be operably coupled to the motor assembly; and
   a worm gear meshingly engaged with the worm, the worm gear directly coupled to the leg support, wherein the worm and the worm gear are configured to transfer rotary motion from the motor assembly to the leg support upon initiation of a force applied to the leg support, the worm gear defining an adapter aperture;
   an adapter disposed within the adapter aperture and at least partially coupled to the worm gear with a key protrusion disposed within a recess of a wall defining the adapter aperture, the adapter configured to operably couple to the leg support.

2. The gearbox assembly of claim 1, further comprising a housing, the worm and the worm gear disposed in the housing.

3. The gearbox assembly of claim 1, wherein the worm gear and worm are configured to be reversible by a second force from the leg support greater than a third force from the gearbox assembly.

4. The gearbox assembly of claim 1, wherein the worm rotates about a first axis and the worm gear rotates about a second axis that is substantially orthogonal to the first axis.

5. A medical assist device comprising:
   a support frame including a support arm extending therefrom;
   a gearbox assembly coupled to the support frame, the gearbox assembly comprising:
      a worm;
      a worm gear meshingly engaged with the worm, the worm gear defining an adapter aperture; and
      an adapter disposed within the adapter aperture and at least partially coupled to the worm gear with a key protrusion disposed within a recess of a wall defining the adapter aperture, the adapter configured to operably couple to a leg support; and
   the leg support directly coupled to the worm gear, the gearbox assembly configured to provide a rotational force to the leg support.

6. The device of claim 5, wherein the gearbox assembly further comprises a housing, the worm and the worm gear disposed in the housing.

7. The device of claim 5, wherein the worm gear and the worm are configured to be reversible by a force from the leg support greater than a force from the gearbox assembly.

8. The device of claim 5, wherein the worm rotates about a first axis and the worm gear rotates about a second axis that is substantially orthogonal to the first axis.

9. The device of claim 5, further comprising a motor assembly operatively coupled to the gearbox assembly to transfer rotary motion to the worm.

* * * * *